US006541513B2

(12) United States Patent
Plata-Salaman et al.

(10) Patent No.: US 6,541,513 B2
(45) Date of Patent: Apr. 1, 2003

(54) CARBAMATE COMPOUNDS FOR USE IN PREVENTING OR TREATING PSYCHOTIC DISORDERS

(75) Inventors: Carlos R. Plata-Salaman, Ambler, PA (US); Boyu Zhao, Lansdale, PA (US); Roy E. Twyman, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/081,761

(22) Filed: Feb. 21, 2002

(65) Prior Publication Data

US 2002/0165272 A1 Nov. 7, 2002

Related U.S. Application Data

(60) Provisional application No. 60/271,889, filed on Feb. 27, 2001.

(51) Int. Cl.⁷ .............................................. A61K 31/27
(52) U.S. Cl. ...................................................... 514/483
(58) Field of Search ......................................... 514/483

(56) References Cited

U.S. PATENT DOCUMENTS 3,265,728 A  *  8/1966  Bossinger et al. .......... 260/482
3,313,692 A  *  4/1967  Bossinger et al. ............ 167/65
5,492,930 A     2/1996  Coffin
6,103,759 A  *  8/2000  Choi et al. ................... 514/489

OTHER PUBLICATIONS

Carlsson, A., et al., *Neurotransmitter Interactions in Schizophrenia –Therapeutic Implications*, Biol. Psychiatry 1999; 46:1388–1395.

Wettstein, J., et al., *Selectivity of Action of Typical and Atypical Anti–Psychotic Drugs as Antagonists of the Behavioral Effects of 1–[2,5–Dimethoxy–4–Iodophenyl]–2–Aminopropane (DOI)*, Prog. Neuroo–Psychophamacol. & Biol. Psychiat, 1999, vol. 23, pp. 533–544.

Abi–Dargham, A., et al., *Increased Baseline Occupancy of $D_2$ Receptors by Dopamine in Schizophrenia*, PNAS, Jul. 2000, vol. 97, No. 14, 8104–8109.

Veenstra–Vanderweele, J. et al., *Pharmacogenetics and the Serotonin System: Initial Studies and Future Directions*, European Journal of Pharmacology 410 (2000), 165–181.

Lieberman, J., et al., *Serotonergic Basis of Antipsychotic Drug Effects in Schizophrenia*, Biol. Psychiatry, 1998, 44, 1099–1117.

Aghajanian, G., et al., *Serotonin Model of Schizophrenia: Emerging Role of Glutamate Mechanisms*, Brain Research Reviews 31, (2000), 302–312.

Yan, Q., *Activation of 5–HT $_{2A/2C}$ Receptors Within the Nucleus Accumbens Increases Local Dopaminergic Transmission*, Brain Research Bulletin, vol. 51, 2000, No. 1, 75–81.

Vollenweider, F., et al., *A Systems Model of Altered Consciousness: Integrating Natural and Drug–Induced Psychoses*, Brain Research Bulletin, vol. 56, No. 5, 2001, 495–507.

Gao, W., et al., *Presynaptic Regulation of Recurrent Excitation by D1 Receptors in Prefontal Circuits*, PNAS, Jan. 2001, vol. 98, No. 1, 295–300.

Meltzer, H., *The Role of Serotonin in Antipsychotic Drug Action*Neuropsychopharmacology, vol. 21, No. 2S, 1999, 106S–115S.

Dowd, C., et al., *1–[4–(3–Phenylalkyl–phenyl]–2–Aminopropanes as 5–HT$_{2A}$ Partial Agonists*, J. Med. Chem., 2000, 43, 3074–3084.

Geyer, M.A., et al., *Pharmacological Studies of Prepulse Inhibition Models of Sensorimotor Gating Deficits in Schizophrenia: A Decade in Review*, Psychopharmacology, 2001, 156, 2–3, 117–154.

Braff, D.L, et al., *Human Studies of Prepulse Inhibition of Startle: Normal Subjects, Patient Groups, and Pharmacological Studies*, Psychopharmacology, 2001, 156, 2–3, 234–258.

(List continued on next page.)

Primary Examiner—Raymond Henley, III

(57) ABSTRACT

This invention is directed to a method for preventing or treating psychotic disorders comprising administering to a subject in need thereof a therapeutically effective amount of a compound selected from the group consisting of Formula (I) and Formula (II):

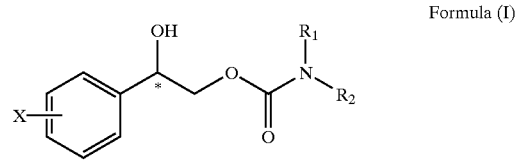

Formula (I)

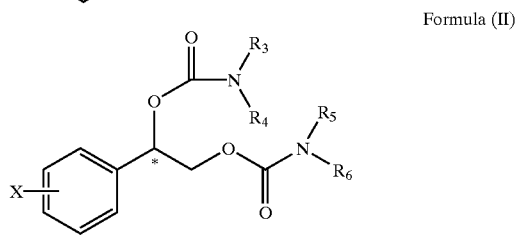

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

22 Claims, No Drawings

OTHER PUBLICATIONS

Cilia, J., et al., *Long-term Evaluation of Isolation-rearing Induced Prepulse Inhibition Deficits in Rats*, Psychopharmacology, 2001, 156, 2–3, 327–337.

Kaplan & Sadock's Comprehensive Textbook of Psychiatry, Seventh Edition, vol. 1, Lippincott Williams & Wilkins: Philadelphia, 2000, p. 825.

Koller, W.C., et al., *Pharmacologic Treatment of Essential Tremor*, American Academy of Neurology, 54, Suppl 4, Jun. 2000, S30–S38.

PCT International Search Report PCT/US02/06119 dated Jul. 2, 2002.

* cited by examiner

CARBAMATE COMPOUNDS FOR USE IN PREVENTING OR TREATING PSYCHOTIC DISORDERS

CROSS REFERENCE TO RELATED APPLICATIONS

This application claims benefit of provisional application Serial No. 60/271,889, filed Feb. 27, 2001, which is hereby incorporated by reference.

FIELD OF THE INVENTION

This invention is directed to a method for use of a carbamate compound in preventing or treating psychotic disorders. More particularly, this invention is directed to a method for use of halogenated 2-phenyl-1,2-ethanediol monocarbamate or dicarbamate compounds for preventing or treating psychotic disorders.

BACKGROUND OF THE INVENTION

Psychotic disorders are those that are predominantly characterized by psychosis. Psychosis is an impairment of mental functioning to the extent that it interferes grossly with an individual's ability to meet the ordinary demands of life. According to the American Psychiatric Association, psychotic means grossly impaired, in terms of reality testing. Such testing would define gross impairment as existing when individuals incorrectly evaluate the accuracy of their perceptions and thoughts and make incorrect inferences about external reality, even in the face of contrary evidence. The term psychotic is also appropriate when behavior is so disorganized that it is reasonable to infer that results of reality testing would indicate an individual as grossly disturbed, for instance, by the existence of markedly incoherent speech without apparent awareness by the person that the speech is not understandable or by the agitated, inattentive and disoriented behavior observed in the phencyclidine psychotic disorder (Diagnostic and Statistical Manual of Mental Disorders, Ed. 4$^{th}$, American Psychiatric Association, Washington, D.C. 1994; Kaplan & Sadock's Comprehensive Textbook of Psychiatry, Seventh Edition, Volume I, Lippincott Williams & Wilkins: Philadelphia, pp. 825, 2000).

Psychotic disorders include, and are not limited to, schizophrenia, schizophreniform disorder, schizoaffective disorder, delusional disorder, brief psychotic disorder, shared psychotic disorder, psychotic disorder due to a general medical condition, substance-induced psychotic disorder or psychotic disorder not otherwise specified (Diagnostic and Statistical Manual of Mental Disorders, Ed. 4$^{th}$, American Psychiatric Association, Washington, D.C. 1994).

Schizophrenia is any of a group of psychotic disorders usually characterized by withdrawal from reality, illogical patterns of thinking, delusions and hallucinations and accompanied in varying degrees by other emotional, behavioral or intellectual disturbances (Schizophrenia, Decision Resources, Inc., December 2000). A lifelong chronic mental illness, schizophrenia exhibits several features including positive and negative symptoms, cognitive deficits, onset in young adulthood and deterioration from the previous level of functioning. Positive symptoms reflect a distortion or excess of normal functions (eg, disorganized speech, delusions, hallucinations). Negative symptoms, on the other hand, reflect a restricted range of normal behavior and emotions (eg, apathy, paucity of speech and incongruity or flattening of emotional responses). Schizophrenia can be presented in various forms depending on the symptoms and signs. The varieties of schizophrenia include paranoid schizophrenia, hebephrenic schizophrenia, catatonic schizophrenia, and undifferentiated schizophrenia as well as post-schizophrenic depression, residual schizophrenia, simple schizophrenia and unspecified schizophrenia.

Increasingly, schizophrenia is conceptualized as a complex biological disorder in which genes play a role (but not an exclusive one) and in which brain development is likely to be abnormal. Multiple abnormalities have been implicated in the pathophysiology of schizophrenia, including serotoninergic dysfunctions and abnormal dopminergic transmission which result in the impairment of sensormotor gating (Aghajanian G K, Marek G J, Serotonin model of schizophrenia: emerging role of glutamate mechanisms, *Brain Res. Rev.*, 2000, 31 (2-3), 302–12; Lieberman J A, Mailman R B, Duncan G, Sikich L, Chakos M, Nichols D E, Kraus J E, Serotonergic basis of antipsychotic drug effects in schizophrenia, *Biol. Psychiatry*, 1998, 44 (11), 1099–117; Veenstra-VanderWeele J, Anderson G M, Cook E H, Pharmacogenetics and the serotonin system: initial studies and future directions, *Eur. J. Pharmacol.*, 2000, 410 (2-3), 165–181; Wen-Jun Gao, Leonid S. Krimer and Patricia S. Goldman-Rakic, Presynaptic regulation of recurrent excitation by D1 receptors in prefrontal circuits, *Proc. Natl. Acad. Sci. USA*, Jan. 2, 2001; 98, 1, 295–300; Anissa Abi-Dargham, Janine Rodenhiser, David Printz, Yolanda Zea-Ponce, Roberto Gil, Lawrence S. Kegeles, Richard Weiss, Thomas B. Cooper, J. John Mann, Ronald L. Van Heertum, Jack M. Gorman and Marc Laruelle, Increased baseline occupancy of $D_2$ receptors by dopamine in schizophrenia, *Proc. Natl. Acad. Sci. USA*, Jul. 5, 2000, 97,14, 8104–8109; and, Geyer, M. A., Krebs-Thomson, K., Braff, D. L., Swerdlow, N. R., Pharmacological studies of prepulse inhibition models of sensormotor gating deficits in schizophrenia: a decade in review, *Psychopharmacology* (Berlin, Ger.), 2001, 156, 2-3, 117–154).

Compounds that have various activities, including exhibiting 5-HT2A receptor antagonism, are effective antipsychotics (Carlsson A, Waters N, Carlsson M L, Neurotransmitter interactions in schizophrenia—therapeutic implications, *Biol. Psychiatry*, 1999, 46 (10), 1388–95). For instance, antipsychotic drugs such as clozapine, olanzapine, quetiapine, risperidone, sertindole, and ziprasidone are potent 5-HT2a receptor antagonists (Meltzer H Y, The role of serotonin in antipsychotic drug action, *Neuropsychopharmacology*, 1999, 21 (2 Suppl), 106S–115S; and, Lieberman J A, Mailman R B, Duncan G, Sikich L, Chakos M, Nichols D E, Kraus J E, Serotonergic basis of antipsychotic drug effects in schizophrenia, *Biol. Psychiatry*, Dec. 1, 1998, 44 (11), 1099–1117).

DOI (1-(2,5-dimethoxy-4-iodophenyl)-2-aminopropane hydrochloride) is an hallucinogen having high affinity and selectivity as an agonist at 5-HT2A/2C receptors (Dowd C S, Herrick-Davis K, Egan C, DuPre A, Smith C, Teitler M, Glennon R A, 1-[4-(3-Phenylalkyl)phenyl]-2-aminopropanes as 5-HT(2A) partial agonists, *J. Med. Chem.*, 2000, 43 (16), 3074–84; Yan Q S, Activation of 5-HT2A/2C receptors within the nucleus accumbens increases local dopaminergic transmission, *Brain Res. Bull.*, 2000, 51 (1), 75–81; Wettstein J G, Host M, Hitchcock J M, Selectivity of action of typical and atypical anti-psychotic drugs as antagonists of the behavioral effects of 1-[2,5-dimethoxy-4-iodophenyl]-2-aminopropane (DOI), *Prog. Neuropsychopharmacol. Biol. Psychiatry*, 1999, 23 (3), 533–44). In the DOI-induced head shake animal model, DOI administration produces dose-related behavioral effects including head shakes. In a dose-dependent manner, antipsychotics such as risperidone, haloperidol, clozapine and olanzapine antagonize the behavioral effects of DOI. Overall, the data shows that antipsychotic agents as a drug class effectively block the effects of DOI with selective activity and that non-antipsychotic drugs were generally inactive (Wettstein J G, Host M, Hitchcock J M, Selectivity of action of typical and atypical anti-psychotic drugs as antagonists of the behavioral effects of 1-[2,5-dimethoxy-4-iodophenyl]-2-aminopropane (DOI), *Prog. Neuropsychopharmacol. Biol. Psychiatry*, April 1999, 23 (3), 533–44).

The prepulse inhibition (PPI) animal model (wherein a reduced startle reflex occurs in dopamine-activated rodents when a startling stimulus is preceded 30 to 500 msec by a weak stimulus or prepulse) and is predictive of clinical antipsychotic potency in a subgroup of schizophrenia patients who have dopaminergic deficits (Vollenweider, Franz X. and Geyer, Mark A., A systems model of altered consciousness: integrating natural and drug-induced psychoses, *Brain Research Bulletin*, 2001, 56, 5, 495–507; Braff, D. L., Geyer, M. A. and Swerdlow, N. R., Human studies of prepulse inhibition of startle: normal subjects, patient groups, and pharmacological studies, *Psychopharmacology* (Berlin, Ger.), 2001, 156, 2-3, 234–258; Geyer, M. A., Krebs-Thomson, K., Braff, D. L. and Swerdlow, N. R., Pharmacological studies of prepulse inhibition models of sensorimotor gating deficits in schizophrenia: a decade in review, *Psychopharmacology* (Berlin, Ger.), 2001, 156, 2-3, 117–154; and, Cilia, J., Reavill, C., Hagan, J. J. and Jones, D. N. C., Long-term evaluation of isolation-rearing induced prepulse inhibition deficits in rats, *Psychopharmacology* (Berlin, Ger.), 2001, 156, 2-3, 327–337).

Because schizophrenia is a disease of multifaceted origin, the different animal models used to predict the efficacy of an antipsychotic drug may suggest that the drug has a specific mechanism of action (for example, affecting serotoninergic or dopaminergic transmission) in different patient populations.

Substituted phenyl alkyl carbamate compounds have been described in U.S. Pat. No. 3,265,728 to Bossinger, et al (hereby incorporated by reference), as useful in treating the central nervous system, having tranquilization, sedation and muscle relaxation properties of the formula:

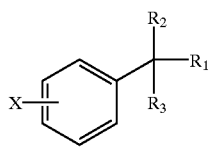

wherein $R_1$ is either carbamate or alkyl carbamate containing from 1 to 3 carbon atoms in the alkyl group; $R_2$ is either hydrogen, hydroxy, alkyl or hydroxy alkyl containing from 1 to 2 carbons; $R_3$ is either hydrogen or alkyl containing from 1 to 2 carbons; and X can be halogen, methyl, methoxy, phenyl, nitro or amino.

A method for inducing calming and muscle relaxation with carbamates has been described in U.S. Pat. No. 3,313,692 to Bossinger, et al (hereby incorporated by reference) by administering a compound of the formula:

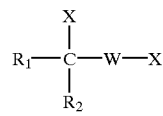

in which W represents an aliphatic radical containing less than 4 carbon atoms, wherein $R_1$ represents an aromatic radical, $R_2$ represents hydrogen or an alkyl radical containing less than 4 carbon atoms, and X represents hydrogen or hydroxy or alkoxy and alkyl radicals containing less than 4 carbon atoms or the radical:

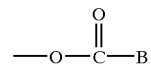

in which B represents an organic amine radical of the group consisting of heterocyclic, ureido and hydrazino radicals and the radical —$N(R_3)_2$ wherein $R_3$ represents hydrogen or an alkyl radical containing less than 4 carbon atoms.

Optically pure forms of halogen substituted 2-phenyl-1,2-ethanediol monocarbamates and dicarbamates have also been described in U.S. Pat. No. 6,103,759 to Choi, et al (hereby incorporated by reference), as effective for treating and preventing central nervous system disorders including convulsions, epilepsy, stroke and muscle spasm; and as useful in the treatment of central nervous system diseases, particularly as anticonvulsants, antiepileptics, neuroprotective agents and centrally acting muscle relaxants, of the formulae:

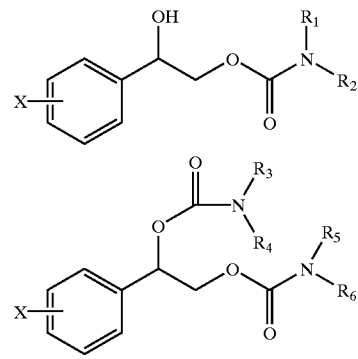

wherein one enantiomer predominates and wherein the phenyl ring is substituted at X with one to five halogen atoms selected from fluorine, chlorine, bromine or iodine atoms and $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. Pure enantiomeric forms and enantiomeric mixtures were described wherein one of the enantiomers predominates in the mixture for the compounds represented by the formulae above; preferably one of the enantiomers predominates to the extent of about 90% or greater; and, most preferably, about 98% or greater.

Halogen substituted 2-phenyl-1,2-ethanediol carbamate compounds of Formula (I) or Formula (II) have not been previously described as useful for preventing or treating psychotic disorders. Recent preclinical studies have revealed previously unrecognized pharmacological properties which suggest that a compound of Formula (I) or Formula (II) is useful in preventing or treating psychotic disorders. Therefore, it is an object of the present invention to teach a method for use of a compound of Formula (I) or Formula (II) in preventing or treating psychotic disorders.

SUMMARY OF THE INVENTION

The present invention is directed to a method for preventing or treating psychotic disorders comprising administering to a subject in need thereof a therapeutically effective amount of a compound selected from the group consisting of Formula (I) and Formula (II):

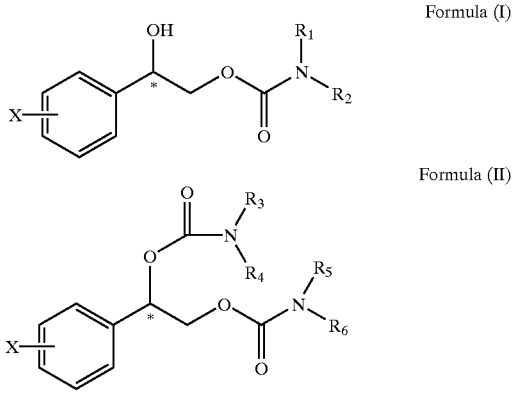

wherein
phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1-C_4$ alkyl; wherein $C_1-C_4$ alkyl is optionally substituted with phenyl (wherein phenyl is optionally substituted with substituents independently selected from the group consisting of halogen, $C_1-C_4$ alkyl, $C_1-C_4$ alkoxy, amino, nitro and cyano).

Embodiments of the invention include a method for preventing or treating psychotic disorders comprising administering to a subject in need thereof a therapeutically effective amount of a pharmaceutical composition comprising a pharmaceutically acceptable carrier and a compound selected from the group consisting of Formula (I) and Formula (II).

Embodiments of the invention include the use of a compound selected from the group consisting of Formula (I) and Formula (II) for the preparation of a medicament for preventing or treating psychotic disorders in a subject in need thereof.

Embodiments of the method include the use of an enantiomer selected from the group consisting of Formula (I) and Formula (II) or enantiomeric mixture wherein one enantiomer selected from the group consisting of Formula (I) and Formula (II) predominates. For enantiomeric mixtures wherein one enantiomer selected from the group consisting of Formula (I) and Formula (II) predominates, preferably, one enantiomer selected from the group consisting of Formula (I) and Formula (II) predominates to the extent of about 90% or greater. More preferably, one enantiomer selected from the group consisting of Formula (I) and Formula (II) predominates to the extent of about 98% or greater.

DETAILED DESCRIPTION OF THE INVENTION

The present invention is directed to a method for preventing or treating psychotic disorders comprising administering to a subject in need thereof a therapeutically effective amount of a compound selected from the group consisting of Formula (I) and Formula (II):

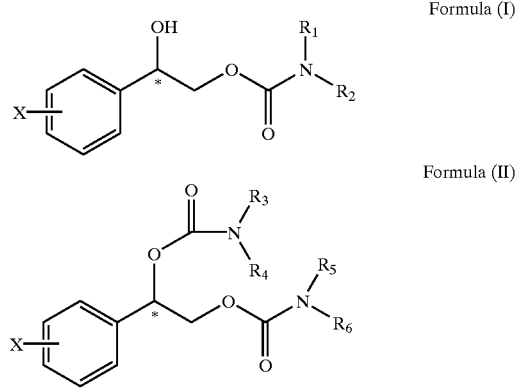

wherein
phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1-C_4$ alkyl; wherein $C_1-C_4$ alkyl is optionally substituted with phenyl (wherein phenyl is optionally substituted with substituents independently selected from the group consisting of halogen, $C_1-C_4$ alkyl, $C_1-C_4$ alkoxy, amino, nitro and cyano).

The present method includes the use of a compound selected from the group consisting of Formula (I) and Formula (II) wherein X is chlorine; preferably, X is substituted at the ortho position of the phenyl ring.

The present method also includes the use of a compound selected from the group consisting of Formula (I) and Formula (II) wherein $R_1$, $R_2$, $R_3$, $R_4$, $R_5$ and $R_6$ are preferably selected from hydrogen.

An embodiment of the present method includes the use of an enantiomer selected from the group consisting of Formula (I) and Formula (II) or enantiomeric mixture wherein one enantiomer selected from the group consisting of Formula (I) and Formula (II) predominates wherein X is chlorine; preferably, X is substituted at the ortho position of the phenyl ring.

The present method also includes the use of an enantiomer selected from the group consisting of Formula (I) and Formula (II) or enantiomeric mixture wherein one enantiomer selected from the group consisting of Formula (I) and Formula (II) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (I) and Formula (II) predominates, preferably, an enantiomer selected from the group consisting of Formula (I) and Formula (II) predominates to the extent of about 90% or greater. More preferably, an enantiomer selected from the group consisting of Formula (I) and Formula (II) predominates to the extent of about 98% or greater.

An embodiment of the present method includes the use of an enantiomer selected from the group consisting of Formula (Ia) and Formula (IIa) or enantiomeric mixture wherein one enantiomer selected from the group consisting of Formula (Ia) and Formula (IIa) predominates:

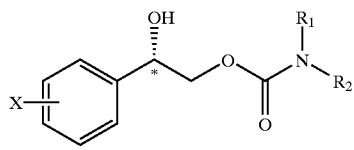

Formula (Ia)

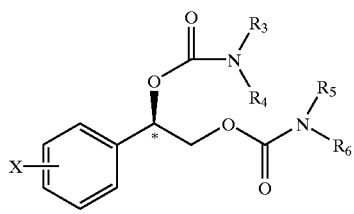

Formula (IIa)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of an enantiomer selected from the group consisting of Formula (Ia) and Formula (IIa) or enantiomeric mixture wherein one enantiomer selected from the group consisting of Formula (Ia) and Formula (IIa) predominates wherein X is chlorine; preferably, X is substituted at the ortho position of the phenyl ring.

The present method also includes the use of an enantiomer selected from the group consisting of Formula (Ia) and Formula (IIa) or enantiomeric mixture wherein one enantiomer selected from the group consisting of Formula (Ia) and Formula (IIa) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (Ia) and Formula (IIa) predominates, preferably, an enantiomer selected from the group consisting of Formula (Ia) and Formula (IIa) predominates to the extent of about 90% or greater. More preferably, an enantiomer selected from the group consisting of Formula (Ia) and Formula (IIa) predominates to the extent of about 98% or greater.

An embodiment of the present method includes a method for preventing or treating psychotic disorders comprising administering to a subject in need thereof a therapeutically effective amount of an enantiomer selected from the group consisting of Formula (Ib) and Formula (IIb) or enantiomeric mixture wherein one enantiomer selected from the group consisting of Formula (Ib) and Formula (IIb) predominates:

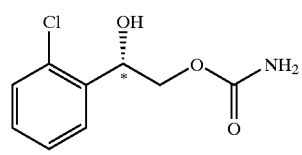

Formula (Ib)

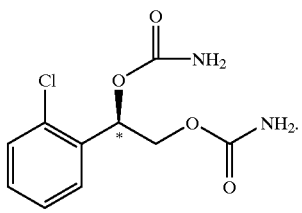

Formula (IIb)

For enantiomeric mixtures wherein one enantiomer selected from the group consisting of Formula (Ib) and Formula (IIb) predominates, preferably, an enantiomer selected from the group consisting of Formula (Ib) and Formula (IIb) predominates to the extent of about 90% or greater. More preferably, an enantiomer selected from the group consisting of Formula (Ib) and Formula (IIb) predominates to the extent of about 98% or greater.

Other crystal forms of the present invention may exist and as such are intended to be included in the present invention.

It is apparent to those skilled in the art that the compounds of the invention are present as racemates, enantiomers and enantiomeric mixtures thereof. A carbamate enantiomer selected from the group consisting of Formula (I), Formula (II), Formula (Ia), Formula (IIa), Formula (Ib) and Formula (IIb) contains an asymmetric chiral carbon atom at the benzylic position, which is the aliphatic carbon adjacent to the phenyl ring (represented by the asterisk in the structural formulae).

Compounds of the present invention may be prepared as described in the previously referenced Bossinger '728 patent (incorporated by reference), Bossinger '692 patent (incorporated by reference) and Choi '759 patent (incorporated by reference).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The present invention contemplates a method for preventing or treating psychotic disorders in a subject in need thereof. Psychotic disorders include, and are not limited to, schizophrenia, schizophreniform disorder, schizoaffective disorder, delusional disorder, brief psychotic disorder, shared psychotic disorder, psychotic disorder due to a general medical condition, substance-induced psychotic disorder or psychotic disorder not otherwise specified. More particularly, schizophrenia includes, and is not limited to, paranoid schizophrenia, hebephrenic schizophrenia, catatonic schizophrenia, undifferentiated schizophrenia, post-schizophrenic depression, residual schizophrenia, simple schizophrenia or unspecified schizophrenia.

An example of the method of the present invention comprises administering to the subject a therapeutically effective amount of a compound selected from the group consisting of Formula (I) and Formula (II) in a pharmaceutical composition comprising a pharmaceutically acceptable carrier and a compound selected from the group consisting of Formula (I) and Formula (II). The method of the present invention also includes the use of a compound selected from the group consisting of Formula (I) and Formula (II) for the preparation of a medicament for preventing or treating psychotic disorders.

Another example of the method of the present invention comprises administering to the subject a therapeutically effective amount of a compound selected from the group consisting of Formula (I) and Formula (II) or a pharmaceutical composition thereof in combination with one or more agents useful in preventing or treating psychotic disorders.

A compound selected from the group consisting of Formula (I) and Formula (II) or pharmaceutical composition thereof may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The therapeutically effective amount of a compound selected from the group consisting of Formula (I) and Formula (II) or pharmaceutical composition thereof may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

The dosages, however, may be varied depending upon the requirement of the subjects (including factors associated with the particular subject being treated, including subject age, weight and diet, strength of the preparation, the advancement of the disease condition and the mode and time of administration) and the use of a particular compound of Formula (I) or Formula (II) or pharmaceutical composition thereof.

Optimal dosages to be administered may be readily determined by those skilled in the art and will result in the need to adjust the dose to an appropriate therapeutic level. The use of either daily administration or post-periodic dosing may be employed. Preferably, a compound of Formula (I) or Formula (II) or pharmaceutical composition thereof for treating psychotic disorders is administered orally or parenterally.

In accordance with the methods of the present invention, a compound of Formula (I) or Formula (II) or pharmaceutical composition thereof described herein may be administered separately, at different times during the course of therapy or concurrently in divided combination or single combination forms. Advantageously, a compound selected from the group consisting of Formula (I) and Formula (II) or pharmaceutical compositions thereof may be administered in a single daily dose or the total daily dosage may be administered via continuous delivery or in divided doses of two, three or four times daily. The instant invention is therefore to be understood as embracing all such methods and regimes of continuous, simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare a pharmaceutical composition of the present invention, a compound of Formula (I) or Formula (II) as the active ingredient is intimately admixed with a pharmaceutical carrier according to conventional pharmaceutical compounding techniques, which carrier may take a wide variety of forms depending on the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition. Revised and Expanded*, Volumes 1–3, edited by Lieberman et al; *Pharmaceutical Dosage Forms: Parenteral Medications*, Volumes 1–2, edited by Avis et al; and *Pharmaceutical Dosage Forms: Disperse Systems*, Volumes 1–2, edited by Lieberman et al; published by Marcel Dekker, Inc.

Preferably, a pharmaceutical composition is in a unit dosage form such as a tablet, pill, capsule, caplet, gelcap, lozenge, granule, powder, sterile parenteral solution or suspension, metered aerosol or liquid spray, drop, ampoule, autoinjector device or suppository for administration by oral, intranasal, sublingual, intraocular, transdermal, parenteral, rectal, vaginal, inhalation or insufflation means. Alternatively, the composition may be presented in a form suitable for once-weekly or once-monthly administration or may be adapted to provide a preparation for intramuscular injection.

In preparing a pharmaceutical composition having a solid dosage form for oral administration, such as a tablet, pill, capsule, caplet, gelcap, lozenge, granule or powder (each including immediate release, timed release and sustained release formulations), suitable carriers and additives include but are not limited to diluents, granulating agents, lubricants, binders, glidants, disintegrating agents and the like. If desired, tablets may be sugar coated, gelatin coated, film coated or enteric coated by standard techniques.

For preparing a solid dosage form, the principal active ingredient is mixed with a pharmaceutical carrier (e.g. conventional tableting ingredients such as diluents, binders, adhesives, disintegrants, lubricants, antiadherents and glidants). Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

In preparing a pharmaceutical composition having a liquid dosage form for oral, topical and parenteral administration, any of the usual pharmaceutical media or excipients may be employed. Thus, for liquid unit dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form. The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

BIOLOGICAL EXPERIMENTAL EXAMPLE

The activities of a compound of Formula (I) and Formula (II) for use in preventing or treating psychotic disorders were evaluated in the following experimental example which is intended to be a way of illustrating but not limiting the invention.

Example 1
DOI-Induced Headshake Model

The administration of DOI to rodents has been used as a model for assessing potential efficacy of an atypical antipsychotic in treating psychosis and schizophrenia in certain patient populations with direct or indirect defects in the serotonin system.

Male NIH Swiss mice weighing 18–21 grams at the time of purchase were obtained from Harlan Sprague Dawley, Inc. (Prattville, Ala.). They were individually housed in wire-mesh cages at an ambient temperature of 21 to 23° C. with an automated 12/12 hour light/dark cycle. All rats had free access to 5001 Rodent Chow (Purina Mills, Brentwood, Mo.) and water except during experimental sessions. The principles of laboratory animal care (NIH publication No. 85–23, revised 1985) were followed.

DOI (purchased from Sigma, St. Louis, Mo.) was dissolved in saline, neutralized to pH ~7.4 and injected ip in a volume of 10 ml/kg body weight. Injection solution was freshly prepared 30–45 minutes before each experiment. Methylcellulose (0.5%, Sigma) was used as oral dosing vehicle. All experiments were performed between 10 am and 4 pm during the day. The mice were fasted the evening before the experiment.

An enantiomer of Formula (Ib), Formula (IIb) or vehicle was orally administered at various concentrations ranging from 10 $\mu$g to 100 mg/kg. The animals were then injected with either saline or DOI (ip, 5 mg/kg) 45 minutes after the administration of either vehicle or an enantiomer of Formula (Ib) or Formula (IIb). Immediately upon DOI administration, the mice were placed in isolated observation cylinders made of a clear polycarbonate (27 cm in diameter and 55 cm deep). The number of randomized headshakes (or twitches) was recorded by an experienced observer using a hand held mechanical counter. Headshake responses were counted in consecutive 10-min periods.

DOI-Induced Headshake Model Analysis

All data are expressed as the mean ±SEM. The average of the headshakes in the vehicle group was expressed as 100%. The DOI-induced headshakes in groups treated with an enantiomer of Formula (Ib) and Formula (IIb) were expressed as percent suppression compared to the vehicle group. Statistical analysis for significant differences was done with the Student t test.

The average of the headshakes in the vehicle group was 7.95±0.2, consistently obtained with 5 mg/kg of DOI (ip) in 382 mice. An enantiomer of Formula (Ib) suppressed the frequency of DOI-induced headshakes dose-dependently with a maximal suppression of 76% at the 100 mg/kg dose. Similar effects, but less potent, were observed in mice treated with an enantiomer of Formula (IIb), having a maximal suppression of DOI-induced headshakes of 43% at 100 mg/kg.

Table 1 summarizes the experimental data (n is the number of animals per group):

TABLE 1

| Dose | % Inhibition | | | | | |
|---|---|---|---|---|---|---|
| | Formula (Ib) | | | Formula (IIb) | | |
| mg/Kg | % Inh. | n | p value | % Inh. | n | p value |
| 0.01 | 11 | 6 | 0.20 | 1 | 6 | 0.50 |
| 0.1 | 20 | 6 | 0.08 | 11 | 6 | 0.25 |
| 1 | 41 | 6 | <0.01 | 4 | 6 | 0.48 |
| 10 | 63 | 10 | <0.001 | 41 | 6 | <0.05 |
| 30 | 58 | 5 | <0.01 | 36 | 6 | <0.05 |
| 100 | 76 | 5 | <0.001 | 43 | 6 | <0.05 |

Example 2
Pre-Pulse Inhibition Model

The restorative effect of an enantiomer of Formula (Ib) on Pre-Pulse Inhibition (PPI) was compared to the disruptive PPI effect of phencyclidine (PCP). PCP is a NMDA antagonist having a wide range of psychotominetic effects in humans. The PPI disruption caused by PCP can be restored by some atypical antipsychotics, such as clozapine, olanzapine, and quetiapine.

Sprague-Dawley-derived male rats were housed in groups of two or three and maintained in a temperature-controlled environment on a 12 h:12 h light cycle. Except during behavioral testing, animals were given free access to food and water. Animals were handled daily for several days to desensitize them to handling stress before behavioral analysis.

An SR-LAB Startle System was used to control auditory stimuli and background noise level and to monitor startle response (±one msec). The average amplitude of the response was the main dependent variable used. Animals (n=20) were grouped according to a baseline mean PPI determined in a brief matching session. Baseline mean PPI testing consisted of 12 noise bursts at 118 dB[A] over a 40 msec time period followed by 3 noise bursts at 12 dB[A] over a 40 msec time period two days before testing with drug.

The rats were pretreated with an enantiomer of Formula (Ib) at 5, 15 and 45 mg/kg (p.o.) 110 minutes prior to treatment with PCP (1.5 mg/kg, s.c.) in saline in a volume of 1 ml/kg. Rats were placed 10 minutes later into individual startle chambers for testing. Clozapine (7.5 mg/kg) was used as a positive control. Testing was done with a 70 dB[A] background noise, followed by a series of startle trials, consisting of several conditions: 1) a 118 dB[A] noise burst over a 40 msec time period, or 2) a 118 dB[A] noise burst over a 40 msec time period preceded by prepulses (118 dB[A] noise bursts over a 20 msec time period) at 100 msec intervals.

Data were collected online simultaneously from multiple startle chambers and analyzed using the Statview 5.0 statistical package. The results from this study showed that acute treatment with an enantiomer of Formula (Ib), up to 45 mg/kg, failed to significantly block the PPI-disruptive effects of PCP. An enantiomer of Formula (Ib) also lacked an orderly dose-dependent reduction in startle magnitude in this study.

While the foregoing specification teaches the principles of the present invention, with examples provided for the purposes of illustration, it will be understood that the practice of the invention encompasses all of the usual variations, adaptations and/or modifications as come within the scope of the following claims and their equivalents.

What is claimed is:

1. A method for preventing or treating psychotic disorders comprising administering to a subject in need thereof a therapeutically effective amount of a compound selected from the group consisting of Formula (I) and Formula (II):

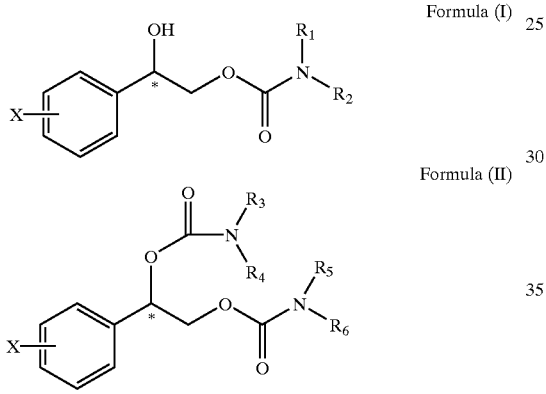

Formula (I)

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

2. The method of claim 1 wherein X is chlorine.

3. The method of claim 1 wherein X is substituted at the ortho position of the phenyl ring.

4. The method of claim 1 wherein $R_1$, $R_2$, $R_3$, $R_4$, $R_5$ and $R_6$ are selected from hydrogen.

5. A method for preventing or treating psychotic disorders comprising administering to a subject in need thereof a therapeutically effective amount of an enantiomer selected from the group consisting of Formula (I) and Formula (II) or enantiomeric mixture wherein one enantiomer selected from the group consisting of Formula (I) and Formula (II) predominates:

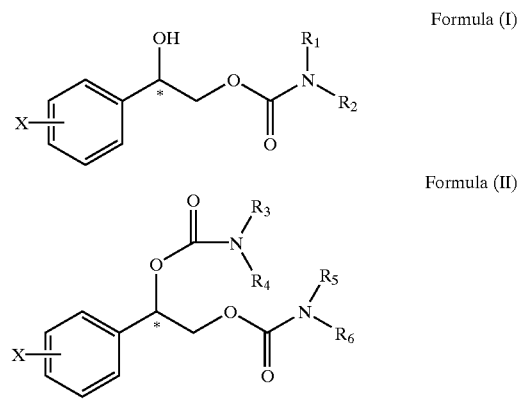

Formula (I)

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

6. The method of claim 5 wherein X is chlorine.

7. The method of claim 5 wherein X is substituted at the ortho position of the phenyl ring.

8. The method of claim 5 wherein $R_1$, $R_2$, $R_3$, $R_4$, $R_5$ and $R_6$ are selected from hydrogen.

9. The method of claim 5 wherein one enantiomer selected from the group consisting of Formula (I) and Formula (II) predominates to the extent of about 90% or greater.

10. The method of claim 5 wherein one enantiomer selected from the group consisting of Formula (I) and Formula (II) predominates to the extent of about 98% or greater.

11. The method of claim 5 wherein the enantiomer selected from the group consisting of Formula (I) and Formula (II) is an enantiomer selected from the group consisting of Formula (Ia) and Formula (IIa):

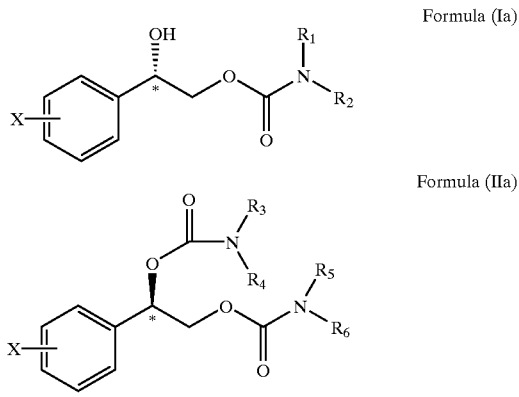

Formula (Ia)

Formula (IIa)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

12. The method of claim 11 wherein X is chlorine.

13. The method of claim 11 wherein X is substituted at the ortho position of the phenyl ring.

14. The method of claim 11 wherein $R_1$, $R_2$, $R_3$, $R_4$, $R_5$ and $R_6$ are selected from hydrogen.

15. The method of claim 11 wherein one enantiomer selected from the group consisting of Formula (Ia) and Formula (IIa) predominates to the extent of about 90% or greater.

16. The method of claim 11 wherein one enantiomer selected from the group consisting of Formula (Ia) and Formula (IIa) predominates to the extent of about 98% or greater.

17. The method of claim 5 wherein the enantiomer selected from the group consisting of Formula (I) and Formula (II) is an enantiomer selected from the group consisting of Formula (Ib) and Formula (IIb):

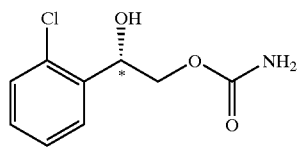

Formula (Ib)

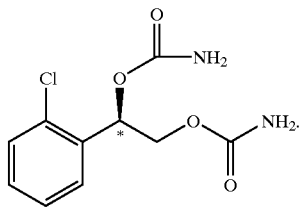

Formula (IIb)

18. The method of claim 17 wherein one enantiomer selected from the group consisting of Formula (Ib) and Formula (IIb) predominates to the extent of about 90% or greater.

19. The method of claim 17 wherein one enantiomer selected from the group consisting of Formula (Ib) and Formula (IIb) predominates to the extent of about 98% or greater.

20. The method as in claim 1 wherein psychotic disorders are selected from schizophrenia, schizophreniform disorder, schizoaffective disorder, delusional disorder, brief psychotic disorder, shared psychotic disorder, psychotic disorder due to a general medical condition, substance-induced psychotic disorder or psychotic disorder not otherwise specified.

21. The method of claim 20 wherein schizophrenia is selected from paranoid schizophrenia, hebephrenic schizophrenia, catatonic schizophrenia, undifferentiated schizophrenia, post-schizophrenic depression, residual schizophrenia, simple schizophrenia or unspecified schizophrenia.

22. The method as in claim 1 wherein the therapeutically effective amount is from about 0.01 mg/Kg/dose to about 100 mg/Kg/dose.

* * * * *